(12) United States Patent
Armoundas et al.

(10) Patent No.: US 9,931,049 B2
(45) Date of Patent: Apr. 3, 2018

(54) METHOD AND APPARATUS FOR THE DETECTION AND CONTROL OF REPOLARIZATION ALTERNANS

(75) Inventors: Antonis Armoundas, Lincoln, MA (US); Eric Weiss, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 289 days.

(21) Appl. No.: 13/509,390

(22) PCT Filed: Nov. 12, 2010

(86) PCT No.: PCT/US2010/056569
§ 371 (c)(1),
(2), (4) Date: Aug. 29, 2012

(87) PCT Pub. No.: WO2011/060284
PCT Pub. Date: May 19, 2011

(65) Prior Publication Data
US 2012/0316611 A1    Dec. 13, 2012

Related U.S. Application Data

(60) Provisional application No. 61/260,897, filed on Nov. 13, 2009.

(51) Int. Cl.
*A61B 5/04* (2006.01)
*A61B 5/0452* (2006.01)
*A61B 5/024* (2006.01)
*A61B 5/00* (2006.01)
*A61N 1/362* (2006.01)
*A61N 1/39* (2006.01)

(52) U.S. Cl.
CPC ........ *A61B 5/0452* (2013.01); *A61B 5/02405* (2013.01); *A61B 5/7275* (2013.01); *A61N 1/3622* (2013.01); *A61N 1/3962* (2013.01)

(58) Field of Classification Search
CPC ..................... A61B 5/0452; A61B 5/02405; A61N 1/3621; A61N 1/3622
USPC .............................................. 607/7; 600/515
See application file for complete search history.

(56) References Cited

U.S. PATENT DOCUMENTS

| | | | |
|---|---|---|---|
| 5,935,082 A * | 8/1999 | Albrecht | A61B 5/0408 600/515 |
| 6,415,174 B1 | 7/2002 | Bebehani et al. | |
| 6,453,191 B2 * | 9/2002 | Krishnamachari | 600/515 |
| 6,782,291 B1 * | 8/2004 | Bornzin et al. | 607/28 |
| 6,915,156 B2 | 7/2005 | Christini et al. | |
| 7,069,069 B2 | 6/2006 | Fishler et al. | |
| 7,233,827 B1 * | 6/2007 | Bornzin et al. | 607/28 |

(Continued)

OTHER PUBLICATIONS

Walker et al. Repolarization alternans: implications for the mechanism and prevention of sudden cardiac death. Cardiovascular Research; 57 (2003); pp. 599-614.*

(Continued)

*Primary Examiner* — Amanda Patton
(74) *Attorney, Agent, or Firm* — Quarles & Brady LLP

(57) ABSTRACT

A method and apparatus are disclosed for preventing heart rhythm disturbances by optimally recording cardiac electrical activity, optimally measuring beat-to-beat variability in the morphology of electrocardiographic waveforms, and using the measured beat-to-beat variability to control the delivery of therapy to the heart.

20 Claims, 8 Drawing Sheets

(56) References Cited

U.S. PATENT DOCUMENTS

| | | | |
|---|---|---|---|
| 7,245,970 B2* | 7/2007 | Zhu et al. | 607/28 |
| 7,336,995 B2* | 2/2008 | Armoundas et al. | 607/9 |
| 7,610,090 B1* | 10/2009 | Hofstadter et al. | 607/27 |
| 7,756,571 B1* | 7/2010 | Farazi | 600/517 |
| 2003/0083709 A1* | 5/2003 | Zhu et al. | 607/27 |
| 2004/0088018 A1* | 5/2004 | Sawchuk et al. | 607/27 |
| 2004/0098061 A1* | 5/2004 | Armoundas et al. | 607/17 |
| 2006/0116596 A1* | 6/2006 | Zhou et al. | 600/516 |
| 2007/0191890 A1* | 8/2007 | Armoundas et al. | 607/9 |
| 2011/0105929 A1* | 5/2011 | Sharma et al. | 600/519 |

OTHER PUBLICATIONS

International Search Report dated Jul. 29, 2011 for International Application No. PCT/US2010/056569.

\* cited by examiner

METHOD AND APPARATUS FOR THE DETECTION AND CONTROL OF REPOLARIZATION ALTERNANS

CROSS-REFERENCE TO RELATED APPLICATIONS

This application represents the U.S. National Stage of International Application No. PCT/US2010/056569, filed Nov. 12, 2010 which claims the benefit of U.S. Provisional Patent Application Ser. No. 61/260,897 filed on Nov. 13, 2009, and entitled "Method and Apparatus for Measuring and Controlling Repolarization Alternans." The foregoing applications are incorporated herein by reference in their-entirety.

BACKGROUND OF THE INVENTION

The field of the invention is systems and methods for preventing heart rhythm disturbances. More particularly, the invention relates to systems and methods for detecting and controlling repolarization alternans such that optional pacing of the heart can be implemented to prevent or suppress adverse cardiovascular events such as sudden cardiac death and occurrences of serious heart rhythm disturbances including ventricular fibrillation, ventricular tachyarrhythmia, and ventricular bradyarrhythmia.

Cardiovascular disease is the greatest cause of morbidity and mortality in the industrialized world. It not only strikes down a significant fraction of the population without warning, but also causes prolonged suffering and disability in an even larger number. Sudden cardiac death ("SCD") is prevalent in the population; however, it is difficult to treat because it is difficult to predict in which individuals it will occur, and often occurs without warning in an out-of-hospital setting. It is widely acknowledged that use of implantable cardioverter defibrillators ("ICDs") has reduced the incidence of SCD in high risk patients.

Clinical trials have suggested that the ICD is effective for secondary prevention of SCD in patients with cardiac arrest due to ventricular fibrillation ("VF"), hemodynamically compromising ventricular tachycardia ("VT"), and syncope with inducible VT. Overall, a number of studies have suggested that patients with a left ventricular ejection fraction ("EF") less than or equal to around thirty-five percent may benefit from ICD therapy. Recently, it has been suggested that patients with coronary artery disease and left ventricular EF less than or equal to around thirty percent derive a mortality benefit from ICD therapy. As a result of such trials, the use of the ICD continues to increase worldwide.

Currently, ICDs are used as an effective therapy for the termination of heart rhythm disturbances. But, the role of ICDs is to deliver electrical impulses to terminate the arrhythmia rather than to prevent its onset. Thus, patients are being subjected to a serious arrhythmia for a period of time until therapy is delivered. Also, delivery of electrical impulses from the ICD may be painful and may damage the heart. There remains, therefore, a need to prevent arrhythmias from initiating rather than treating them with what may be much higher energy electrical pulses after the arrhythmias have been initiated.

Arrhythmias such as ventricular tachycardia and fibrillation are often caused by an electrical mechanism called reentry. FIGS. 1A-1D illustrate that reentry involves a loop-like path of electrical activation circulating through a region of heart tissue, reentering regions that had been previously activated in prior loops. In early ischemic arrhythmias, ventricular tachycardia and fibrillation have been shown to depend on reentrant excitation. Although reentrant excitation is thought to underlie a variety of benign and malignant cardiac rhythms, descriptions of the mechanisms that are involved in the development of reentry remain obscured. A major factor leading to the genesis of ventricular fibrillation during ischemia is dispersion of refractoriness. Dispersion of refractoriness is a measure of non-homogeneous recovery of excitability in a given mass of cardiac tissue. A tissue is called refractory when it cannot be re-stimulated until it has recovered. In normal myocardium the excitability is strictly proportional to the duration of repolarization. Reentry is the most likely mechanism of arrhythmia facilitated by enhanced dispersion of repolarization. The elements that are most often represented in the experimental or clinical models of arrhythmias attributed to reentry include non-uniform conduction, non-uniform excitability, and non-uniform refractoriness.

Ischemia alters refractoriness through its effects on resting potential and action potential duration. These effects are non-uniform during regional ischemia because of local variations in blood flow and diffusion of substrate and metabolites across the ischemic boundary. The resulting non-uniformity in refractoriness undoubtedly contributes to the increased vulnerability of an ischemic heart to fibrillation. An important mechanism for enhancing dispersion of refractory period is alternation of the action potential from beat to beat.

Action potential alternans involves an alternating sequence in which the shape of the action potential, which is the wave-like pattern of variation of a cell's transmembrane potential, associated with an individual cardiac cell changes on an every other beat basis. If the duration of the action potential alternates on an every other beat basis, then the duration of refractory period also alternates in duration because the refractory period is generally roughly comparable to the duration of the action potential. Thus, action potential alternans creates a situation in which a region of the myocardium has a long refractory period on an every other beat basis. On these alternate beats, a region with action potential alternans can create islands of refractory tissue that can cause fractionation of activation wavefronts. Thus, action potential alternans, which generally occurs in diseased tissue, can promote the development of reentry.

The presence of action potential alternans can be detected in an electrocardiogram ("ECG") as an ST segment or T-wave alternans ("TWA"), which is also referred to as repolarization alternans ("RA"). In the surface electrocardiogram, repolarization alternans has been correlated with the presence of ventricular vulnerability to arrhythmias in humans. As used herein, the term "repolarization alternans" includes any change in the morphology of the ST segment or T-wave of the electrocardiogram occurring on an every other beat basis.

Computer simulations of cardiac conduction processes have predicted the relationship between the presence of electrical alternans and enhanced susceptibility to the onset of reentrant rhythm disturbances. Specifically, the simulated ECGs have shown electrical alternans in myocardial cells that have refractory periods that exceed a threshold cycle length, resulting in a corresponding subpopulation of cells that can be at most activated every second beat. This process leads to wavefront fractionation, thus being the predisposing factor to reentrant ventricular dysrhythmias.

Recent studies have demonstrated that the presence of microvolt level repolarization alternans, which is generally not visible upon visual inspection of the electrocardiogram, but detectable using advanced signal processing techniques, is associated with an increased risk of ventricular arrhythmias and sudden cardiac death. Moreover, in ECG tracings obtained from Holter monitoring, there has been evidence that repolarization alternans persist for long periods before the onset of an unstable heart rhythm like ventricular tachycardia or ventricular fibrillation. Thus, in both computer simulations and experimental reports, repolarization alternans have been shown to increase its magnitude in the stage preceding a malignant heart rhythm like ventricular fibrillation.

Clinically, an RA test is classified as indeterminate if there is significant noise or ectopy. In early studies, indeterminate RA tests were assumed to have no predictive capability and were excluded from final analysis. However, because indeterminate RA tests account for the majority of non-negative tests, more recent studies have grouped indeterminate tests together with positive tests as abnormal. The high death rate in the indeterminate group clearly indicates that an indeterminate test has an unfavorable prognosis, but the nature of this risk is unclear. This raises the possibility that an indeterminate test may actually predict arrhythmic risk. Although this may seem counterintuitive, it is possible that patients with non-sustained alternans or frequent premature ventricular contractions ("PVCs") are prone to ventricular arrhythmias even if the estimation of RA in these patients does not accurately classify them as being at high risk for arrhythmic events. Recent analyses of indeterminate tests have concluded that such patients are at high risk for tachyarrhythmic events, suggesting that the prognostic value of RA may be improved by reclassification of indeterminate tests.

Furthermore, there remains a need to improve the accuracy for estimation and classification of RA tests in order to reduce the false positive and false negative rates currently found. By addressing such a need, the clinical utility of RA testing for risk stratification can be improved upon.

Detection of RA further involves identifying the optimal locations in the heart to place a number of sensing leads that would maximize the probability of detecting RA. It further involves proportionately scaling the intracardiac alternans voltage and noise thresholds to account for these greater amplitudes. Failure to scale the alternans voltage and noise thresholds in this manner leads to increased sensitivity but reduced specificity for alternans detection when comparing intracardiac to body surface leads.

A reentrant waveform can be terminated by electrical pacing that is initiated within a specific period during reentrant excitation. This process gives rise to a new wave whose front collides with and annihilates the reentrant wave. A pacing stimulus occurring before complete recovery may induce graded responses and hence prolong the action potential and refractoriness. When the leading edge of the reentrant wavefront revisits this area it cannot reenter. This circumstance results in bi-directional block and the termination of reentry. Thus, the use of pacing as a method to terminate ventricular arrhythmias may result in the termination of reentry and VF; changes in the shape, or position of the shape, of the center of the activity and induction of different reentrant waveforms or a focal pattern of repetitive activation; changes in the "exit" pathway, or in the direction, of the activity; or resetting of the activity and persistence of the same reentry.

In light of the foregoing considerations, there remains a need to prevent arrhythmias from initiating rather than treating the arrhythmias with what may be much higher energy electrical pulses after the arrhythmias have been initiated. Thus, it would be highly desirable to be able to prevent arrhythmias from starting rather than terminating them after their initiation by administration of an electrical shock. There also remains a need to more accurately estimate the initiation of cardiac arrhythmias, so that they can be prevented before initiation occurs.

SUMMARY OF THE INVENTION

The present invention overcomes the aforementioned drawbacks by providing a system and method for suppressing cardiac arrhythmias, such as ventricular arrhythmias, before their initiation by detecting and controlling repolarization alternans in real-time. In particular, a method for preemptively suppressing a cardiac arrhythmia in a patient's heart with an implanted device configured to generate electrical impulses is provided. Cardiac electrical signals are detected from the patient's heart and electrical alternans, such as repolarization alternans, is measured in those signals. One or more parameters of the electrical alternans are then estimated from the measured alternans. For example, alternans voltage, alternans noise, and a K-score are estimated. These parameters are estimated taking into consideration levels of random and colored noise. Moreover, these parameters are estimated from a beat sequence in which abnormal heart beats have been replaced with a median of the even or odd normal beats when the abnormal beat is itself an even or odd heart beat, respectively. An electrical therapy plan is calibrated using the estimated parameters and is delivered to the patient's heart in the form of electrical impulses when the severity and probability of an imminent cardiac arrhythmia is determined.

It is an aspect of the invention to provide a method for preemptively suppressing heart rhythm disturbances. Such a method includes detecting, and optionally recording, cardiac electrical activity; measuring beat-to-beat variability in the cardiac electrical activity, such as electrical alternans; and using the beat-to-beat variability to control therapy to reduce the likelihood of the heart rhythm disturbances.

It is another aspect of the invention to provide a method for delivering electrical therapy to a patient's heart. The electrical therapy includes, for example, delivering electrical impulses to the heart. The electrical impulses may be controlled to alter the variability in the inter-beat interval or the diastolic interval. A number of heart rhythm disturbances, including but not limited to ventricular tachyarrhythmias, bradyarrhythmias, and fibrillation can be preemptively suppressed by use of the disclosed method. Notably, beat-to-beat variabilities in the patient's cardiac cycle are measured in real-time, such that an onset of the aforementioned heart rhythm disturbances can be predicted before the disturbances occur. The predicted disturbance is then preemptively suppressed by delivering the appropriately tailored electrical therapy, which is calibrated using information from the measured beat-to-beat variabilities.

It is yet another aspect of the invention to provide a method in which the electrical activity of the heart is recorded from at least one passive electrode specifically arranged on or within the heart.

It is yet another aspect of the invention to provide a method in which the measuring of electrical alternans is performed in an implanted device. The electrical therapy may also delivered by an implanted device, and this implanted device may optionally serve as a cardiac pacemaker or a cardiac cardioverter-defibrillator.

It is yet another aspect of the invention to provide a method in which the implantable device is capable of generating electrical stimulating pulses of specified increasing energies and applying the pulses to body tissue at specified adjusted times appropriate for substantially preventing the heart rhythm disturbance.

It is yet another aspect of the invention to provide a method in which the measuring of electrical alternans further includes identifying periods when there is an increased probability that a heart rhythm disturbance may occur. Periods of increased susceptibility to life-threatening arrhythmias may be characterized by increased levels of repolarization alternans. In these identified periods, therapy may be delivered.

It is yet another aspect of the invention to provide a method for reducing the morbidity and mortality resulting from heart rhythm disturbances and the pain and complications associated with the termination of heart rhythm disturbances, for example, by administering low energy electrical impulses to the heart. Additionally, the morbidity and mortality resulting from heart rhythm disturbances may be reduced by administering high energy electrical impulses, such as occurs when an implanted cardioverter-defibrillator ("ICD") discharges to terminate ventricular tachycardia or fibrillation.

It is yet another aspect of the invention to provide a method for the application of early electrical therapy that utilizes an ICD to provide a significant improvement in preventing SCD. Currently, state of the art ICDs identify an abnormal heart rhythm based on the detection of its rate and morphology. However, failure or delay in detecting ventricular tachycardia or ventricular fibrillation are common. False detection of ventricular tachycardia or ventricular fibrillation is also a concern. In addition, the implications of an intervention after the development of an abnormal rhythm are not exactly known. Energy delivery in the myocardium, even if it succeeds to revert the heart rhythm to normal, is not an unharmful intervention either in short or long term of the cardiac function. Usually, an increase in the energy delivered is required in repetitive shocks, and as a result, a possible accumulative damage in the cardiac tissue occurs. Moreover, depending on the type of the abnormal heart rhythm, an ICD may not succeed to lead the heart back to a normal rhythm.

It is yet another aspect of the invention to provide a method for detecting and estimating repolarization alternans with more sensitivity and specificity than achievable with previous systems and methods. This method provides improved accuracy for screening patients for implantable cardioverter-defibrillator ("ICD") implantation, thereby increasing the probability that such devices will not be needlessly placed. The method also provides improved accuracy for determining periods of increased likelihood of the occurrence of an arrhythmia and, therefore, the delivery of preventive therapy from an ICD.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

An apparatus and method for preventing heart rhythm disturbances are provided and involve detecting, and optionally recording, cardiac electrical activity from electrodes placed in or on the patient's body proximate the patient's heart. The cardiac electrical activity is monitored and beat-to-beat variability in the cardiac electrical activity is measured. A variety of algorithms have been described in the art for measuring variability, including those described, for example, by D. S. Rosenbaum, et al., in "Electrical Alternans and Vulnerability to Ventricular Arrhythmias," *N. Engl. J. Med.*, 1994; 330:235-241; by D. R. Adam, et al., in "Fluctuations in T-Wave Morphology and Susceptibility to Ventricular Fibrillation," *J. Electrocardiol.*, 1984; 17:209-218; and by J. M. Smith, et al., in "Electrical Alternans and Cardiac Electrical Instability," *Circulation*, 1988; 77:110-121. An improved method for more accurately detecting beat-to-beat variabilities is provided, as will be described below in detail. The measured beat-to-beat variability in the heart's electrical activity provides information on the likelihood of heart rhythm disturbances occurring. This information is used to control therapy so that the heart rhythm disturbances may be prevented from occurring.

Figure 1A:
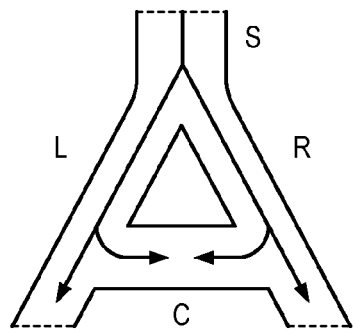
FIGS. 1A-1D are graphic illustrations of the role of a unidirectional block in reentry.
Figure 1B:
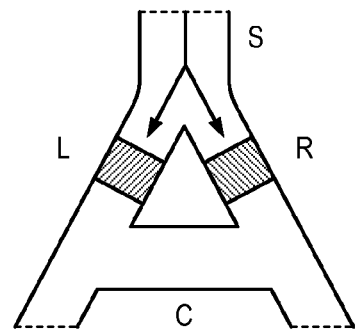
Figure 1C:
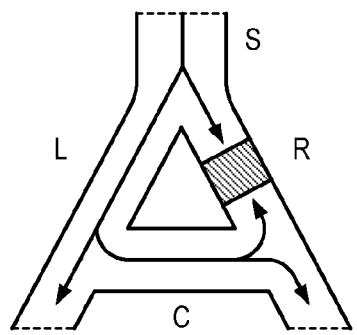
Figure 1D:
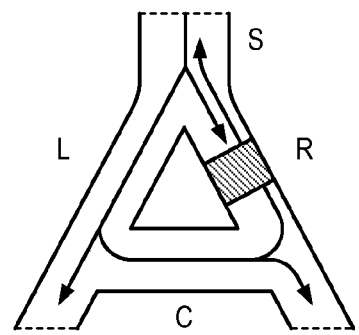
Figure 2:
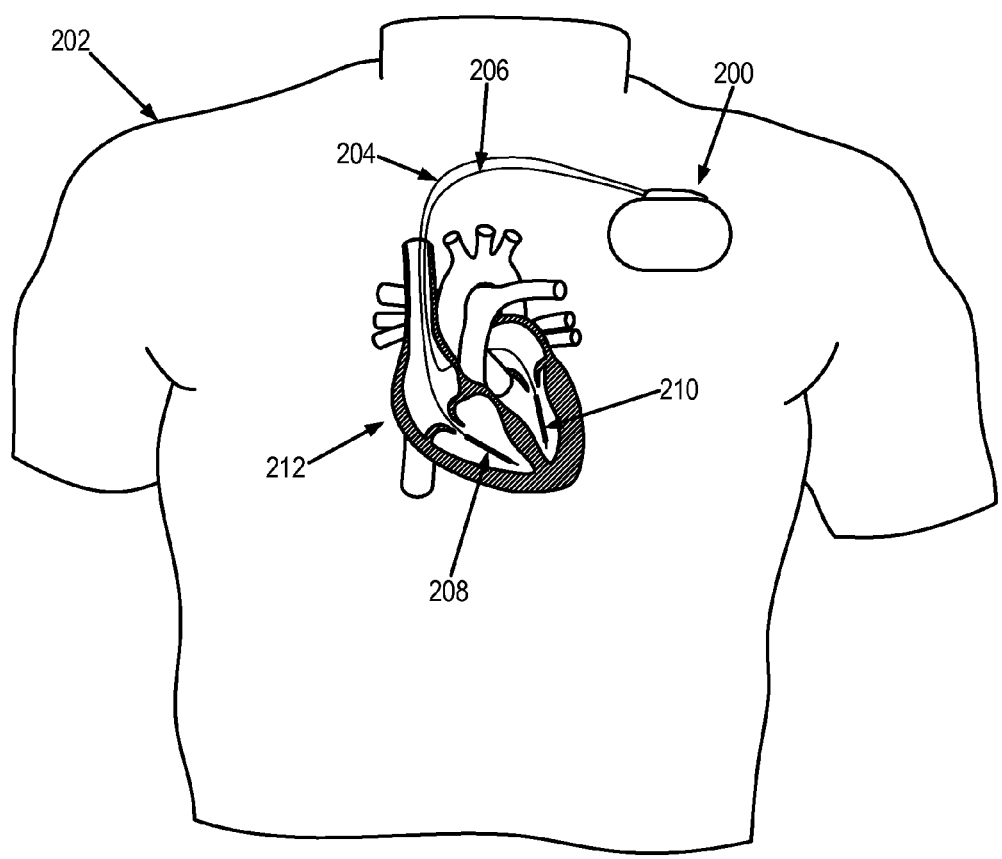
FIG. 2 is an illustration of an exemplary implantable cardioverter-defibrillator in accordance with the present invention.

An exemplary electrical cardioversion-defibrillation device, such as an implantable cardioverter-defibrillator ("ICD") 200 is illustrated in FIG. 2. The ICD 200 is implanted in the pectoral region of the chest of a patient 202, and is configured to include a plurality of connector ports for connection to various implantable catheter and other electrodes, as is known in the art. For example, electrode leads 204 and 206 are shown extending from the ICD 200 to catheter electrodes 208 and 210, which are passed into the desired anatomical areas of a patient's heart 212. The specific configuration of the electrodes of the defibrillation system is dependent upon the requirements of the patient as determined by the physician; however, an exemplary lead configuration for use with the disclosed method is described below. Detection of repolarization alternans ("RA") includes identifying optimal locations in the heart to place a number of sensing leads that would maximize the probability of detecting the RA.

The electrical activity of the heart is detected and recorded from at least one pair of passive electrodes, each one placed in the right atrium, right ventricle, left atrium, left ventricle, and the coronary sinus. Such passive electrodes may be both placed in either the right atrium or the right ventricle, or the left ventricle or the coronary sinus of the heart. Alternatively each of the two passive electrodes can be placed in any of the four chambers of the patient's heart. Three pairs of passive electrodes can also be placed in such a way that a pair includes one electrode placed in the right ventricle and the other in the distal coronary sinus; one electrode in the proximal coronary sinus and the other in the distal coronary sinus; or one electrode in the right ventricle and the other in the proximal coronary sinus. Three pairs of passive electrodes can also be placed in such a way that a pair includes one electrode placed in the left ventricle and the other in the distal coronary sinus; one electrode in the proximal coronary sinus and the other in the distal coronary sinus; or one electrode in the left ventricle and the other in the proximal coronary sinus. Intracardiac electrocardiographic signals are recorded through a processor unit (not shown in FIG. 2) integrated in the ICD device 200.

Signals may be acquired in a continuous, real-time manner and may be analyzed in selected "beat sequences." Specifically, a beat sequence includes a selected number, N, of time-points, or beats, including a currently detected beat and the N−1 preceding beats. By way of example, N=128; however, it should be apparent that other values for the selected number of beats in a beat sequence can be readily adapted. Repolarization alternans estimates may be obtained from electrograms recorded from the intracardiac electrodes described above.

Because unipolar electrocardiograms integrate a large volume of cardiac tissue, they provide less spatial localization of cardiac events than bipolar electrocardiograms; unipolar electrocardiograms are also more susceptible to motion artifact than bipolar electrocardiograms.

Under much testing, to date, there has been substantially no statistical difference in alternans voltage detection between unipolar and far-field bipolar lead configurations on any of the disclosed intracardiac catheters. On the other hand, the far-field bipolar alternans voltage detection and K-score calculation has been more robust than the near-field bipolar alternans voltage detection. Alternans noise tends to be larger as the size of the sensing vector on each catheter increases, with unipolar sensing exhibiting the highest alternans noise level.

Therefore, because the far-field bipolar leads are, generally, statistically equivalent to the unipolar leads for RA detection, and because the benefits of far-field intracardiac sensing include better spatial localization of sensing and less susceptibility to noise than unipolar sensing vectors, far-field bipolar intracardiac leads are generally preferred for detecting RA. However, in some circumstances the far-field bipolar intracardiac leads may be less favorable.

As mentioned previously, in addition to the aforementioned far-field leads, three RV-CS leads spanning the heart can be constructed, formed between the right ventricle, the distal coronary sinus, and the proximal coronary sinus. In general, it is contemplated that far-field bipolar intracardiac leads provide an improved sensitivity of alternans detection compared to body surface electrocardiograms alone. Moreover, it is contemplated that the aforementioned RV/LV-CS leads provide an improved sensitivity to alternans detection compared to leads in the right ventricle, left ventricle, coronary sinus, and epicardial space alone.

Preliminary R-wave time-points, or beats, are obtained by applying a software-based QRS detection algorithm to signals recorded by the cardiac electrodes. Preliminary QRS detections are refined and abnormal beats, such as premature ventricular complexes ("PVCs") and aberrantly conducted beats, are identified using a template-matching QRS alignment algorithm.

For example, for each new beat, an 80 ms window centered at the peak of the QRS complex may be formed from the preliminary beat detection. An isoelectric PR segment may be automatically subtracted as a zero amplitude reference point by estimating the mean voltage in a 10 ms window preceding the start of each QRS complex. A median QRS template is generated from all "normal" QRS complexes across the previous beats in the beat sequence and the current beat is aligned to the QRS template by cross-correlating the current beat with the median beat. Cross-correlation is repeated twice for each new QRS complex to ensure proper QRS alignment. A current beat may be considered "abnormal" if its correlation coefficient is less than a threshold value, for example 0.95, or if the preceding R-to-R ("RR") interval was, for example, at least ten percent shorter than the mean RR interval of a selected number of the previous beats, such as, for example, the previous seven beats. An exemplary beat classification decision matrix is presented in Table 1.

TABLE 1

| Case | Correlation Criterion | ΔRR Interval Criterion | Abnormal Beats | Justification |
|---|---|---|---|---|
| A | <0.95 | <−10% | 3 beats: previous, current, next | Premature Ventricular Contraction |
| B | <0.95 | ≥−10% | 1 beat: current | Aberrantly conducted sinus beat (i.e. bundle branch block) |
| C | ≥0.95 | <−10% | 3 beats: previous, current, next | Supraventricular |
| D | ≥0.95 | ≥−10% | 0 | Normal |

Applying the decision matrix in Table 1, every time a beat is identified that does not meet the RR interval criterion, such as for a premature ventricular complex, the current, preceding, and subsequent beats are all labeled "abnormal." When only the correlation criterion is not met, such as for an aberrant beat, only the current beat is labeled "abnormal."

Once all abnormal beats are identified in a beat sequence, each abnormal beat is replaced with a median odd or even template beat on a lead-by-lead basis depending on whether the abnormal beat was an even or odd beat. The median odd or even template beat is derived from the odd or even "normal" beats, respectively, in the beat sequence.

Repolarization interval boundaries for RA analysis are independently determined for each of the intracardiac unipolar leads and intracardiac bipolar leads due to variability in the morphology, as well as the timing of, the T-wave between leads. Continuing with this example, each beat, initial T-wave boundaries are established using a rate-based T-wave window formula, in which the window begins, for example, 100 ms after the R-wave if the previous RR interval was greater than 770 ms; 40 ms plus 7.8 percent of the RR interval after the R-wave if the previous RR interval was between 320 and 770 ms; and 65 ms after the R-wave if the previous RR interval was less than 320 ms. The T-wave window ends, for example, 500 ms after the R-wave if the previous RR interval was greater than 770 ms, or ends at sixty-five percent of the RR interval if the previous RR interval was shorter than 770 ms.

Then, T-wave boundaries are detected lead-by-lead by performing linear baseline adjustment across the T-wave window, using, for example, the approximate T-wave boundaries described above; squaring the T-wave; integrating the T-wave power; and determining new and more accurate T-wave boundaries at timings corresponding to, for example, one percent and ninety-nine percent of the signal power, respectively. Still continuing with this example, QRS boundaries are detected using the above method, using an initial window extending from, for example, 50 ms prior to the QRS detection point to either 80 ms after the QRS detection point, or to the beginning of the T-wave, whichever is shorter. The repolarization interval is calculated as the end of the QRS complex to the end of the T-wave. Boundaries between the ST segment and T-wave are not calculated due to significant ST segment elevations during acute coronary artery occlusion.

Spectral alternans analysis may be performed on a beat-by-beat basis for all beats in a given beat sequence using, for example, a 512-point power spectrum to improve the frequency-domain resolution. To account for the spatial variability of RA, spectral analysis may be independently performed for each lead. Repolarization alternans indices may be estimated as follows:

$$V_a(\mu V) = \sqrt{P_a - \mu_n} \quad \text{Eqn. (1);}$$

where $V_a$ is the alternans voltage in microvolts ($\mu W$); $P_a$ is the alternans peak, which is the peak in the aggregate power spectrum corresponding to 0.5 cycles/beat; and $\mu_n$ is the mean of the spectral noise, the mean being estimated from a predefined aggregate power spectrum noise window (for example, between 0.43-0.46 cycles/beat). An alternans K-score may be calculated as follows:

$$K_{score} = \frac{P_a - \mu_n}{\sigma_n}; \quad \text{Eqn. (2)}$$

where $\sigma_n$ is the standard deviation of the spectral noise, the standard deviation also being estimated from a predefined aggregate power spectrum noise window (for example, between 0.43-0.46 cycles/beat).

The alternans voltage is a direct measure of the presence of alternans, while the alternans K-score is a measure of the statistical significance of the alternans voltage. For each lead, alternans is estimated on a beat-by-beat basis using a rolling beat window that is shifted, for example, one beat at a time. Exemplary beat windows may have the same total length as the beat sequence, for example, 128 beats.

Repolarization alternans estimated from body surface electrocardiograms in humans is deemed "positive" when both of the following criteria are met: (i) $K_{score} \geq 3.0$, and (ii) $V_a \geq 1.0$ microvolt at rest. However, because intracardiac unipolar and bipolar signals are larger in amplitude than body surface signals, it is necessary to proportionately scale the intracardiac alternans voltage thresholds to account for these greater amplitudes. Failure to scale the voltage thresholds in this manner will result in an increased sensitivity, but reduced specificity for alternans detection when comparing intracardiac to body surface leads, thereby introducing bias into the detection process.

A method is, therefore, provided in which an intracardiac alternans voltage threshold can be determined on an case-by-case basis by first calculating an amplitude scale factor for each intracardiac lead, and then scaling the body surface alternans voltage threshold by this scale factor. Briefly, for each catheter lead, the signal amplitude may be calculated as the square root of the mean signal power between 1-50 Hz. The amplitude scale factor for each lead can then be calculated as the ratio of the mean signal amplitude, divided by the mean signal amplitude recorded from all of the cardiac electrodes. The alternans voltage threshold for each catheter lead is then calculated as the amplitude scale factor multiplied by the body surface threshold of 1.0 microvolt.

By way of example, positive RA is determined to be present in a signal detected by a given lead within a beat analysis window when the K-score exceeds a value of 3.0, and the alternans voltage exceeds the alternans voltage threshold as estimated for that lead. For example, if fewer than ninety percent of the beats within the analysis window are "normal" beats, then the data segment is labeled as indeterminate.

Figure 3A:
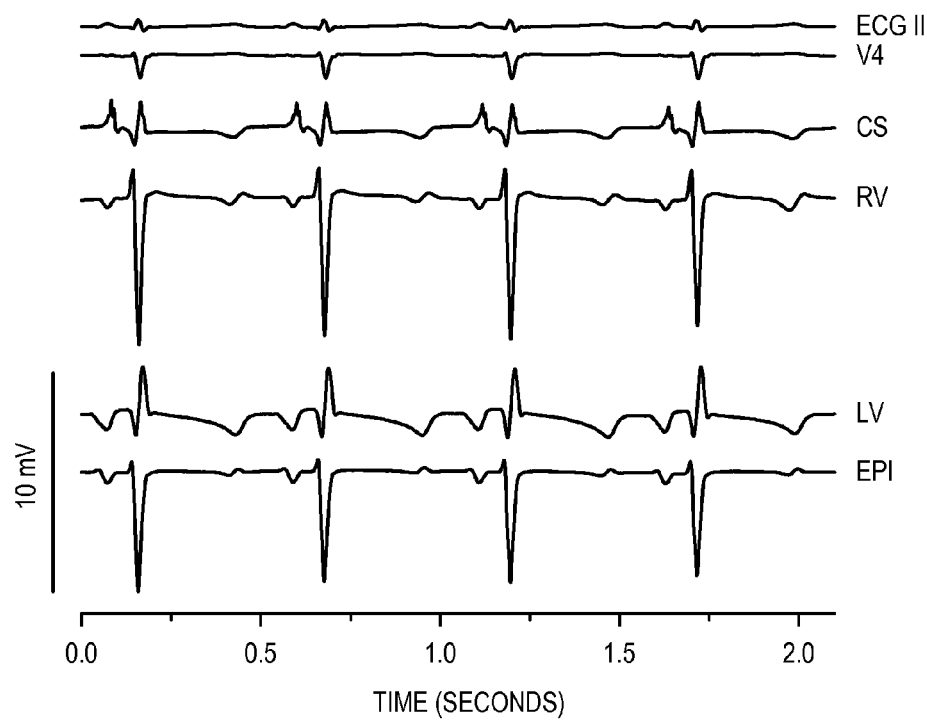
FIG. 3A is a graphic representation of exemplary electrocardiogram signals recorded using the exemplary lead configuration described herein.
Figure 3B:
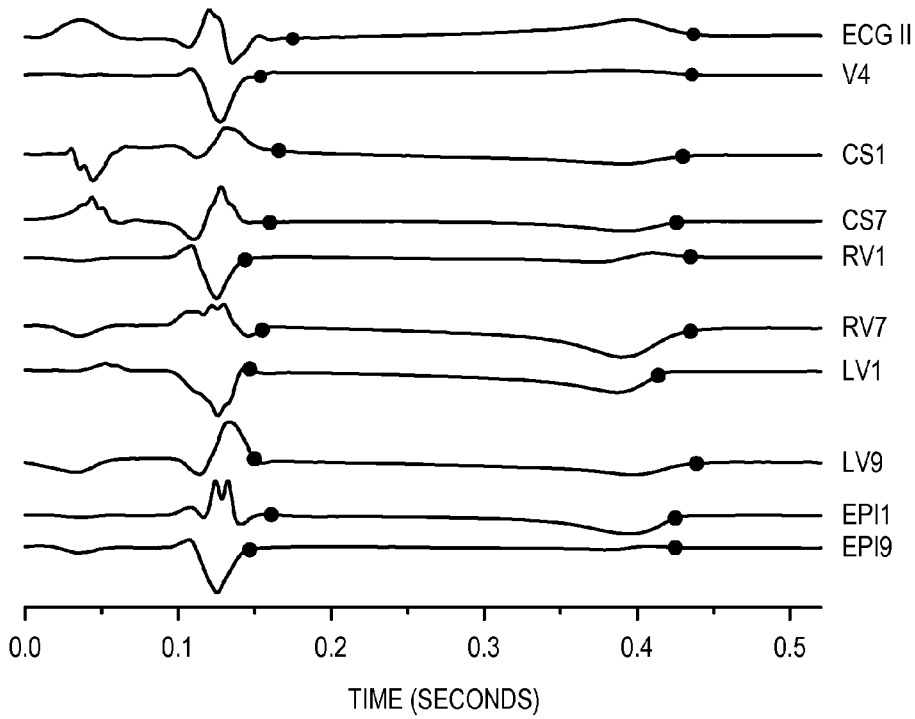
FIG. 3B is a graphic representation of exemplary repolarization interval boundaries in electrocardiogram signals in which the two black circles in each lead signal correspond to repolarization interval begin and end points, respectively.

In FIG. 3A, representative examples of unipolar intracardiac electrocardiograms are illustrated. Because of the variability in T-wave morphology and timing among leads, repolarization interval boundaries are automatically and independently detected for each lead. FIG. 3B shows not-to-scale examples of body surface and unipolar intracardiac electrocardiograms demonstrating that repolarization interval boundaries are accurately delineated for further RA analysis, and that these boundaries vary significantly on a lead-by-lead basis.

Figure 4A:
FIG. 4A is a graphic illustration of exemplary R-wave based, time aligned points in a T-wave, from which repolarization alternans can be estimated.
Figure 4B:
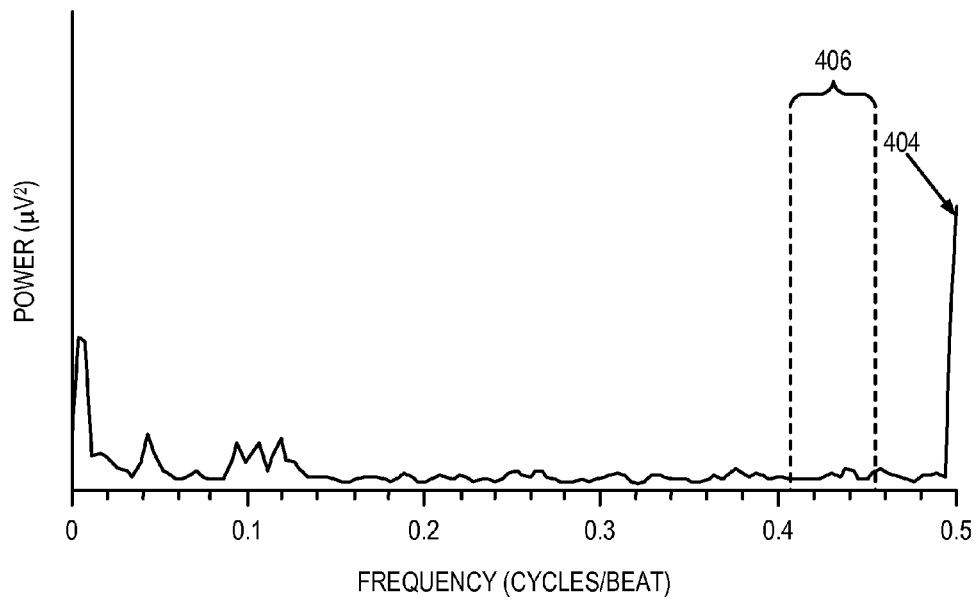
FIG. 4B is a graphic illustration of an exemplary beat sequence power spectrum indicating the presence of alternans at 0.5 cycles/beat and a noise band window at 0.431-0.460 cycles/beat.

For alternans spectral analysis, an N-beat, or N-point, fast Fourier transformation (FFT) algorithm is employed, where N is the number of beats, or time points, in the beat sequence. By way of example, and referring to FIGS. 4A and 4B, given a series of ECG points 402 (FIG. 4A), repolarization alternans is estimated from the "alternans peak" 404, which is the amplitude of the FFT power spectrum corresponding to a frequency of 0.5 cycles/beat; and the mean, $v_n$, and standard deviation, $\sigma_n$, of the spectral noise estimated in a predefined noise window, for example from the noise band 406 ranging over 0.431-0.460 cycles/beat, as illustrated in FIG. 4B.

Previous methods for estimating RA rely on algorithms that replace abnormal beats in a beat sequence with an average beat calculated from the beat sequence. Replacing an abnormal beat with an average beat may not cause significant change in the alternans voltage when compared to the alternans voltage with no abnormal beats. However, this is only the case when the abnormal beat does not alter the alternating sequence of the T-wave morphologies, or in other words, does not provoke phase resetting.

In the presence of phase resetting, it was discovered to be detrimental to replace an abnormal beat with an average beat because when phase resetting occurs, the power of the spectrum shifts to neighboring frequencies. The magnitude of this effect is particularly evident when phase resetting occurs in the middle of a beat sequence, thereby causing a loss of the alternating pattern, which subsequently results in destructive interference of the power spectrum amplitude at the alternans frequency.

As discussed above, the disclosed method replaces an abnormal beat with a median of the even or odd normal beats, depending on whether the abnormal beat was an even or odd beat in the beat sequence. The overall average and overall median point replacement of an abnormal beat can result in ten percent error of the estimated K-score, whereas replacement with an appropriate odd or even median beat substantially reduces such variation, resulting in around a one percent error for each abnormal beat index.

The error in estimating the alternans peak is significantly smaller when using the odd-even median replacement compared to the overall average or the overall median methods. Moreover, similar trends can be seen for the alternans voltage and the alternans noise. However, when using the odd-even median replacement method, because the noise decreases at a faster rate than the alternans peak, the K-score increases as the percent of abnormal beats increases. This K-score increase happens because the substitution of abnormal beats with an odd or even median reduces the variability of the time series and, thus, reduces the amplitude of the noise. The opposite effect happens when an abnormal beat is replaced with the overall average or the overall median.

At the maximum allowable ten percent threshold of abnormal beats, the error in estimating the alternans voltage using odd-even median replacement is around five percent, while the error is 21-23 percent using the overall median or the overall average methods, respectively. This represents around a four-fold reduction in the alternans voltage error using the odd-even median replacement versus either the overall median or the overall average. Using the same ten percent threshold, the error in estimating the K-score is around three percent using the odd-even median replacement, while the error is around nineteen percent using the overall median or the overall average. Thus, around a seven-fold reduction in the K-score error is achieved when using the odd-even median replacement method compared to either the overall median or the overall average.

Overall, if the abnormal beat frequency is less than, for example, sixty percent, replacement of an abnormal beat with an odd or even median produces significantly smaller errors compared to replacement with the overall average or overall median beat. As the percentage of bad points exceeds the sixty percent mark, however, the odd-even median replacement increases the K-score error compared to the other two methods, which suggests that beyond this percentage, the number of false positives compared to the other two methods would be higher.

Given that phase resetting causes a shift in the spectral power from the alternans frequency to neighboring frequencies, it is contemplated that different estimation methods should be implemented in the presence of phase resetting. By way of example, given a spectral resolution of 0.0039 cycles per beat, the last five frequencies in the power spectrum of a beat sequence are 0.4844, 0.4883, 0.4922, 0.4961, and 0.5000 cycles/beat, with the last frequency being the alternans frequency. In the presence of phase resetting, the error in the estimation of the alternans voltage increases when using the last one or two frequencies in the spectrum as the abnormal beat moves towards the center of the beat sequence. Conversely, when employing the last three, four, or five frequencies in the estimation, the error in the alternans voltage becomes smaller, with the three-frequency estimation providing the smallest error. It is also noted that the error of the mean and standard deviation of the alternans noise is slightly increased in the presence of phase resetting.

Therefore, at a spectral resolution of 0.0039 cycles per beat, in the presence of phase resetting, K-score estimation using the sum of the power-spectrum amplitude at frequencies greater than 0.4922 cycles/beat is more accurate than using only the power spectrum amplitude at 0.5 cycles/beat for the majority of the abnormal beat indices.

In another embodiment, in body-surface electrocardiographic recordings, all three of the following conditions must be met in order to classify an alternans test as positive: (1) $K_{score} \geq 3.0$, (2) alternans voltage$\geq 1.9$ microvolts, and (3) alternans noise$\leq 1.8$ microvolts.

Figure 5:
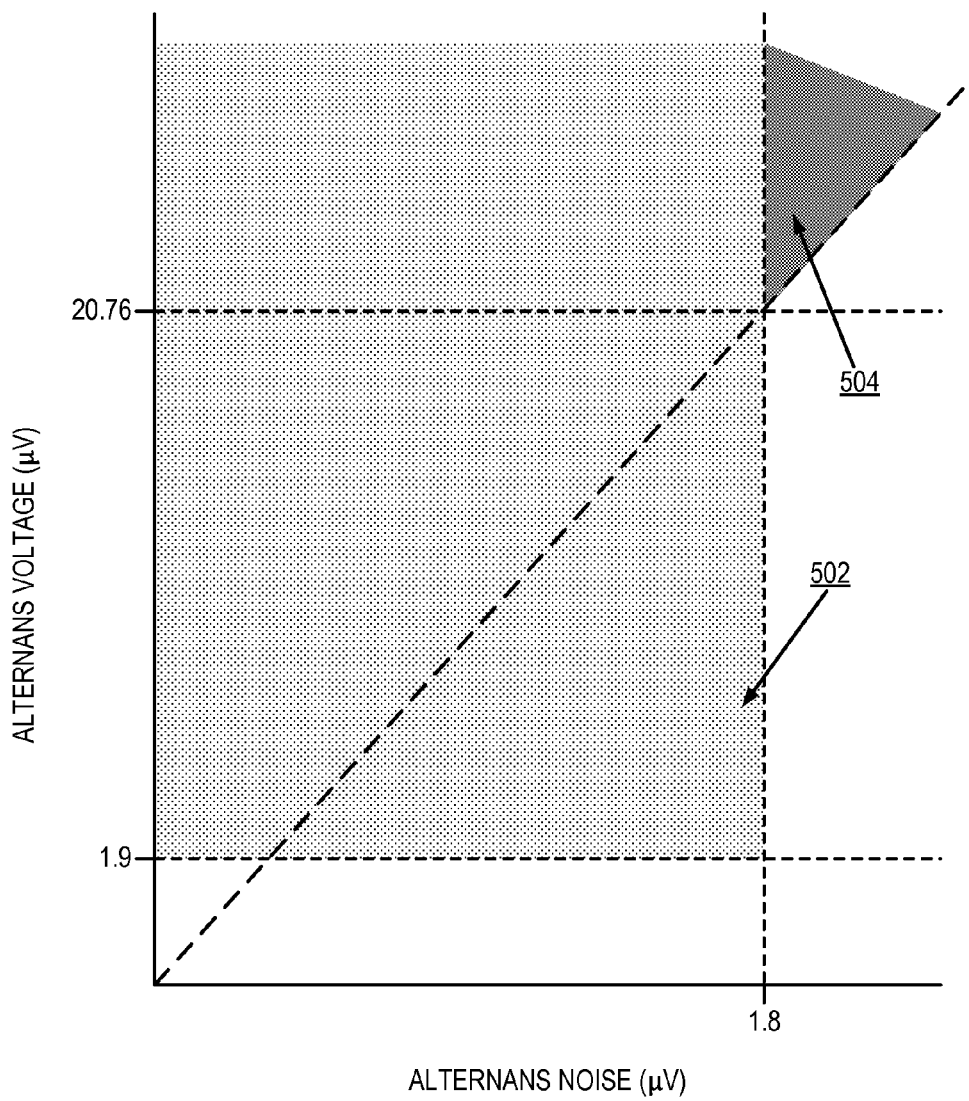
FIG. 5 is a graphic illustration of a traditional zone and a new zone for positive repolarization alternans results based on values of alternans voltage and alternans noise.

The mean alternans voltage and mean alternans noise can be related through a linear relationship determined by linear regression techniques. This linear relationship is as follows:

$$\overline{V}_a = 11.533 \cdot \mu_a - 0.0023 \qquad \text{Eqn. (3);}$$

where $\overline{V}_a$ is the mean alternans voltage and $\mu_a$ is the mean alternans noise. In light of this linear relationship, consideration should be given to the amplitude of the mean alternans noise when the alternans voltage threshold is used to determine whether statistically significant alternans is present. Traditionally, in body-surface electrocardiographic recordings, alternans is considered present when the alternans voltage exceeds, for example, 1.9 microvolts and the alternans noise is less than, for example, 1.8 microvolts, as illustrated in FIG. 5 as zone 502. However, in the absence of random noise, statistically significant alternans can be considered present when the alternans voltage exceeds the alternans noise by a factor, for example, of at least 11.53 under the conditions described in Eqn. (3), regardless of the alternans noise level. Thus, as shown in FIG. 5, a new area 504 for alternans diagnosis that was previously regarded as a region of indeterminate alternans detection is established.

In this new detection area 504, where the alternans noise exceeds the 1.8 microvolts threshold used in this example, formerly indeterminate alternans tests can be considered positive when the alternans voltage exceeds the alternans noise by at least a factor of 11.53. This factor gives rise to a new alternans voltage threshold that is greater than 20.76 microvolts when the alternans noise is greater than 1.8 microvolts.

Figure 6:
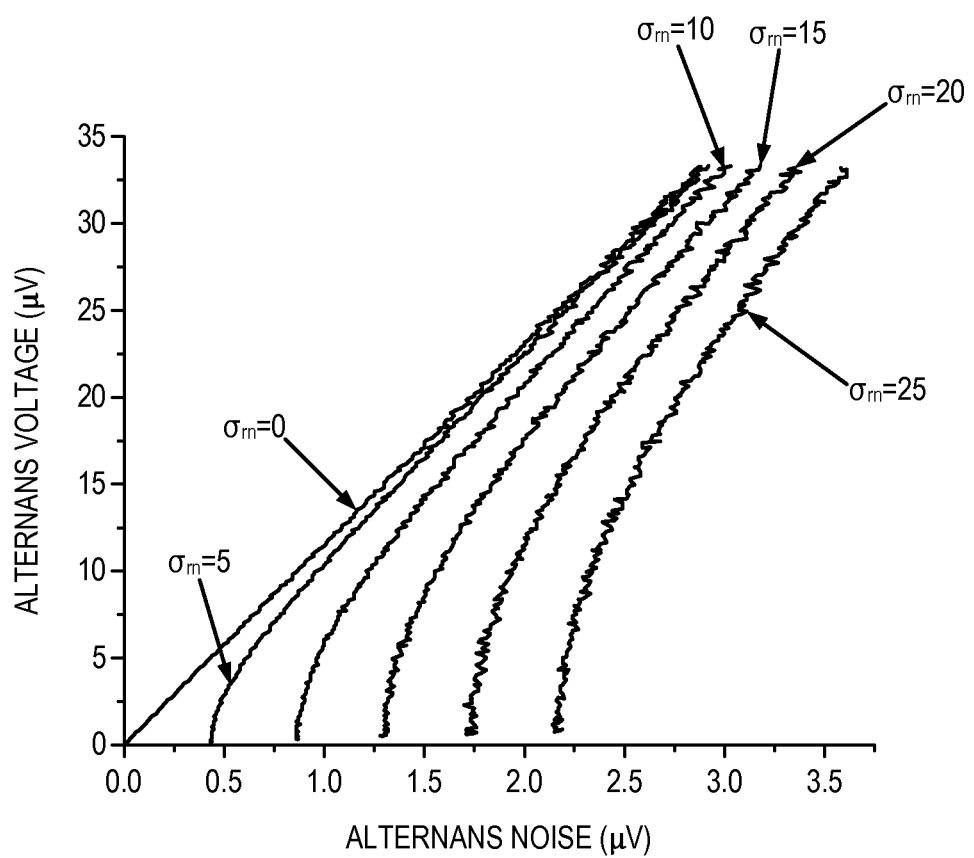
FIG. 6 is an exemplary plot of alternans voltage as a function of the alternans noise for distinct random noise values.

The presence of random noise markedly affects the K-score when the noise level exceeds roughly twenty-five percent of the signal level. As the amplitude of the random noise increases, the alternans voltage that yields a K-score of 3.0 must also increase. Thus, for random noise of 2-3 microvolts, the amplitude of the alternating time series must be at least 0.245-0.370 microvolts to result in a K-score of 3.0. As shown in FIG. 6, by plotting the alternans voltage as a function of the alternans noise at multiple random noise values, $\sigma_{rn}$, it can be seen that only at $\sigma_{rn}=0$ is this relationship substantially linear.

Because random noise is directly quantifiable using a variety of techniques, a new alternans voltage threshold can be formed as a function of alternans noise for any value of random noise using an adapted version of Eqn. (3). For example, for random noise values of five microvolts, and for alternans noise of 1.8 microvolts, the corresponding alternans voltage threshold is 20.29 microvolts.

Thus, consideration should be given not only to the amplitude of the mean alternans noise but also to the random noise level when the alternans voltage threshold is used to determine statistically significant alternans. When the alternans voltage exceeds a threshold determined by the alternans noise and random noise levels, alternans can be considered present even when the alternans noise exceeds, for example, 1.8 microvolts. Clinically, this corresponds to the case in which formerly indeterminate alternans in the presence of elevated noise can still be diagnosed as positive alternans, when the alternans voltage is sufficiently large.

Therefore, it is contemplated that this threshold adjustment may reduce the number of indeterminate results due to excessive noise.

Alternans estimation can be affected by colored noise, potentially leading to an increased probability of a false positive result. As the colored noise frequency approaches the alternans frequency of 0.500 cycles/beat, and as the colored noise amplitude increases, the alternans voltage becomes overestimated and the probability of a false positive detection increases. Therefore, methods for quantifying colored noise sources, specifically those due to respiration, near the alternans frequency of 0.500 cycles/beat are desirable for eliminating problematic data segments, and, thus, reducing the false positive detection rate.

Colored noise can also affect the alternans estimation by corrupting the alternans noise estimation. As the colored noise frequency enters into the alternans noise frequency band, the alternans noise is overestimated, the alternans voltage is underestimated, and the probability of a false negative detection increases. Therefore, methods for quantifying colored noise sources, specifically those due to respiration, near the alternans noise band are desirable for prohibiting respiratory contributions on the noise band, and, thus, reducing the false negative detection rate.

Figure 7:
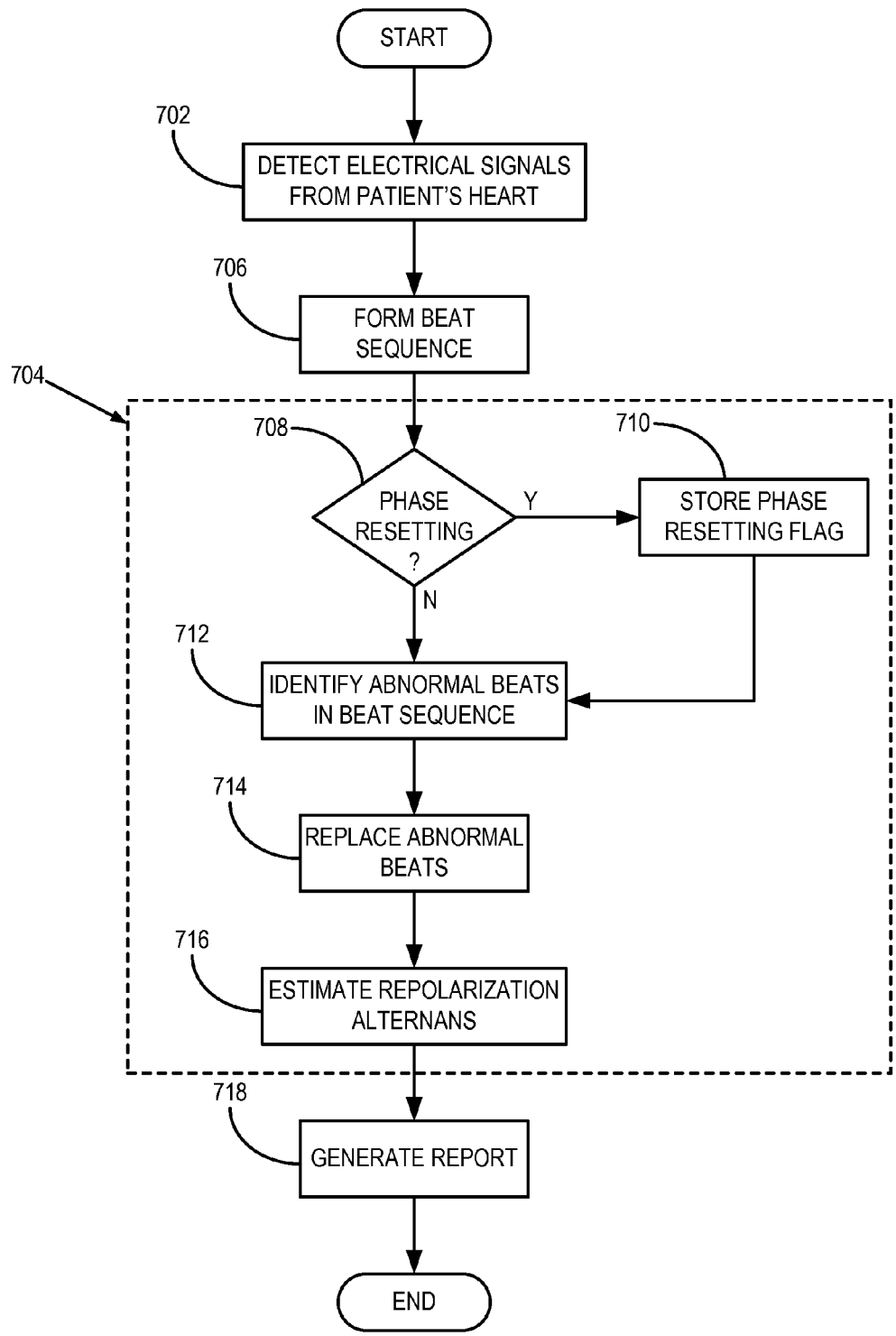
FIG. 7 is a flowchart setting forth the steps of an exemplary method for determining and measuring the presence of repolarization alternans in accordance with the present invention.

Referring particularly now to FIG. 7, a flowchart setting forth the steps of an exemplary method for detecting repolarization alternans ("RA") is illustrated. The method begins with the detection of electrical signals from the patient's heart, as illustrated at step 702. For example, electrical signals can be detected using intracardiac leads positioned on, in, or around the patient's heart and connected to an implantable cardioverter-defibrillator ("ICD"). Bipolar leads used by the ICD may be formed, for example, as follows: between one passive electrode placed in the right ventricle and another in the distal coronary sinus; between one passive electrode in the proximal coronary sinus and another in the distal coronary sinus; and between one passive electrode in the right ventricle and another in the proximal coronary sinus.

Electrical signals are recorded from the intracardiac leads in real-time as the patient's heart beats. Beat-to-beat variability in the patient's cardiac activity is measured, as indicated generally at 704. As discussed above, the beat-to-beat variability measurement is performed in an implanted device such as an ICD or cardiac pacemaker. Such devices contain miniature microprocessors capable of performing the computations necessary for the measurement. A variety of algorithms for computing the variability can be implemented. The beat-to-beat variability is, for example, ventricular repolarization alternans. As discussed above, repolarization alternans has been well established as a predictor of the development of ventricular arrhythmias.

First, a beat sequence is formed by aggregating the electrical signals from each lead for a selected number of beats, as indicated at step 706. For example, 128 beats are selected to form the beat sequence. This beat sequence is continuously updated as more electrical signals are recorded from the patient's heart. A determination is then made as to whether there is phase resetting in the beat sequence, as indicated at decision block 708. If phase resetting is present, then this information is stored for guiding subsequent processing steps, as indicated at step 710.

For each beat sequence, abnormal beats are identified, as indicated at step 712. As discussed above in detail with respect to Table 1, a decision matrix may be utilized to assess whether a current beat is abnormal or normal. When a beat is identified as abnormal, it and potentially adjacent beats are labeled, for example, as such in accordance with the decision matrix in Table 1. When all of the beats in a beat sequence have been identified as normal or abnormal, the abnormal beats are replaced, as indicated at step 714. For example, if the abnormal beat being replaced is an even or odd beat in the beat sequence, then it is respectively replaced with an even or odd median beat. The even or odd median beat is respectively calculated as the median of all normal even or odd beats in the beat sequence. Alternatively, the abnormal beat can be replaced with the median of all the normal beats in the beat sequence, or the average of all the normal beats in the beat sequence. It is noted, however, that if phase resetting is present, it is detrimental to replace an abnormal beat with the average or the median of the normal beats in the beat sequence. Moreover, if the even or odd median beat is used to replace a bad beat, it is desirable that the number of replaced beats in a beat sequence not exceed a percentage of the total number of beats in that sequence, for example, sixty percent.

Repolarization alternans parameters are estimated from the beat sequence with abnormal beats replaced, as indicated at step 716. Exemplary parameters include the alternans voltage, the alternans noise, and the K-score. When phase resetting is present, alternans may be estimated by summing the spectral values at all frequencies above greater than a threshold frequency that depends on the number of FFT points used to estimate the power spectrum. For example, alternans estimated from frequencies greater than 0.4922 cycles/beat in a 128-point FFT provides the most accurate approach for estimating the alternans voltage and K-score when phase resetting is likely to occur.

A report is generated using the estimated repolarization alternans information, as indicated at step 718. This report indicates the presence of repolarization alternans in the beat sequence, and can be utilized either in a diagnostic setting to indicate the suitability of a patient for implantation of an ICD, or in a therapeutic setting to direct and control of electrical pacing of the heart in order to prevent the onset of cardiac arrhythmias. The level of repolarization alternans can be quantified by, for example, measurement of the alternans voltage, alternans noise, and measurement of the alternans ratio, or K-score, in one or more of the intracardiac leads. Threshold values of these RA parameters are established and employed for body surface electrocardiographic signals, such as 1.9 microvolts for the alternans voltage, a value of 3.0 for the K-score alternans ratio, and 1.8 microvolts for the alternans noise. However, there are instances where these threshold values are not adequate in determining the presence of repolarization alternans. Thus, in accordance with the present invention, it has been recognized that, in many clinical situations, the use of dynamic thresholding is more appropriate. Examples of such dynamic thresholding are presented below.

Because the amplitude of alternans noise greater than, for example, 1.8 microvolts has a significant effect on alternans voltage estimation, the alternans voltage threshold is scaled to the level of the alternans noise when it exceeds the threshold value of 1.8 microvolts, so that the number of indeterminate RA tests are reduced. This scaling of the alternans voltage threshold is indicated above in Eqn. (3).

Because the amplitude of random noise has a significant effect on the alternans voltage, noise, and K-score estimation, the alternans voltage, noise, and K-score threshold values are considered as functions of random noise levels. This allows for a more accurate assessment of repolarization alternans in the presence of significant random noise.

Colored noise that coincides with or is near the alternans frequency may lead to a false positive result, while colored noise that falls on the noise band may lead to a false negative result. Therefore, the effect of the heart and respiratory rate on the alternans noise and alternans peak estimation are estimated and utilized to assign a probability to whether an RA test is a true positive or negative. For example, when there is significant colored noise at the alternans frequency, the alternans voltage will be overestimated. Therefore, in this instance the probability of a true positive should be scaled back. Similarly, when there is significant respiratory induced colored noise in the noise band, alternans voltage will be underestimated. Therefore, in this instance, the probability of a true negative should be scaled back.

As noted above, the disclosed method for detecting repolarization alternans can be implemented to guide the control of pacing signals applied to the heart so that cardiac arrhythmias can be prevented before they initiate. That is, given the high correlation between the presence of RA and the incidence of ventricular tachycardia and ventricular fibrillation, and having developed a method to estimate RA in real-time from intracardiac or body surface signals, a system and method that can be used to suppress RA by delivering clinically appropriate electrical therapy is provided.

The stimulator in an ICD is programmed to be capable of dynamically delivering pacing pulses on a beat-to-beat basis. Each pacing pulse is triggered upon detection of an ECG waveform (the R-wave or the peak of the T-wave). The R- or the T-wave detection channel and detection threshold (in millivolts) are user-adjustable. Customizable digital trigger output channels can be independently configured by the user, and each trigger output channel can be independently coupled to the QRS complex (R-wave triggered) or to the T-wave (T-wave triggered) and can deliver a timed digital pulse with one millisecond resolution. Triggered pacing can be delivered from a single trigger output channel, or from multiple channels either simultaneously or sequentially. For each output, the user can select the coupling interval with respect to the R- or T-wave (in milliseconds), the pulse amplitude (in milliampere), the pulse width (in milliseconds), and whether to trigger on an every beat, every even beat, or every odd beat basis.

By way of example, pacing pulses coupled to the R-wave are selected because these pacing pulses fall during the absolute refractory period of the ventricular myocardium and, therefore, do not result in myocardial excitation. For example, bipolar current pulses are delivered from the distal leads 1-2 of a decapolar catheter, with 3 mm spacing, in the RV, LV, or CS.

The effects of the pacing vector spacing, which is the distance between the active electrodes that form a given lead, on alternans voltage and K-score is now discussed. By way of example, R-wave triggered pacing pulses are delivered from electrodes on the RV catheter every-other-beat with an amplitude of −5 mA, pulse width of 10 ms, and R-wave coupling interval of 10 ms. The pacing vector spacing affects the alternans voltage. For example, difference in alternans voltage between baseline and triggered conditions increases as the pacing vector spacing increases. The difference in K-score between baseline and triggered data segments also increases as the pacing vector spacing increases.

Figure 8:
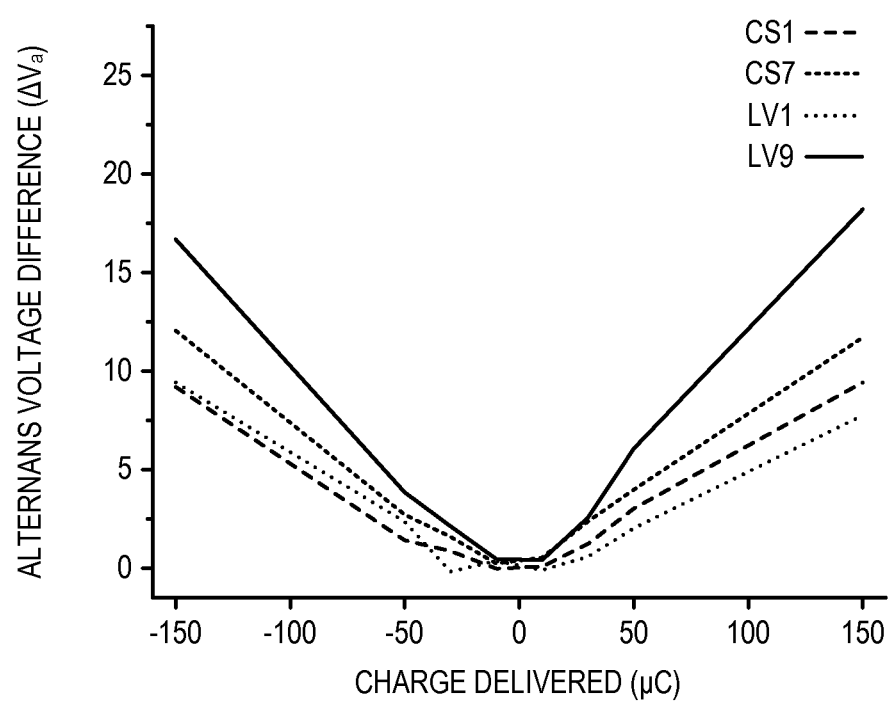
FIG. 8 is an exemplary plot of the effects of delivered charge during triggered pacing on alternans voltage.

The effect of the charge delivered during triggered pacing on alternans voltage is illustrated in FIG. 8. Specifically, the change in alternans voltage ($\Delta V_a$) between baseline and triggered data segments as a function of delivered charge, from −150 to 150 microcoulombs is shown. R-wave triggered pacing pulses are delivered from two RV electrodes with 3 mm spacing every-other-beat with a 10 ms R-wave coupling interval. Both the delivered charge and the lead used independently affect alternans voltage. For example, the change in alternans voltage observed in LV and CS leads (FIG. 8) increases as the magnitude of the delivered charge increases.

It is contemplated that pacing during the absolute refractory period does not increase the PVC rate, or the incidence of arrhythmias or conduction abnormalities. This suggests that pacing during the absolute refractory period does not make the heart pro-arrhythmic, a significant implication for determining whether this form of pacing can be used in a clinical setting.

It is contemplated that identifying the phase of ECG complexes during alternans can be used to design and deliver clinically appropriate electrical therapy for suppressing RA. In such an instance, the morphology of the beats will be determined and discriminated. Using this information, an appropriate pacing protocol will be designed and applied to the heart, such that differences between even and odd beats during alternans is disrupted.

For example, amplitude or morphology discrimination of at least one passive lead may be used to determine whether the amplitude of the odd beats in a time series of points is larger than the amplitude of the even beats in the series, or vice versa. Another example of amplitude discrimination may use all the ECG samples involved in the RA estimation in order to determine the difference between the even and odd beats. In one such particular example, amplitude discrimination is provided by integrating the area under the ECG signal that will be used in the RA estimation for all odd and all even beats, separately, to determine the amplitude difference between odd and even beats. In another such example, amplitude discrimination is provided by integrating the area under the absolute value of the ECG signal that will be used in the RA estimation for all odd and all even beats, separately, to determine the amplitude difference between odd and even beats.

Controlled therapy using repolarization alternans includes the delivery of electrical impulses to the heart through electrodes in or on the heart, for example, the intracardiac leads connected to an ICD as discussed above. It is contemplated that the electrical impulses cause excitation of the cardiac tissue. It is noted, however, that the energy of these impulses is far less than the energy associated with delivery of a defibrillation shock to terminate ventricular fibrillation. Thus, these impulses are not expected to cause unwanted damage to the heart tissue. By pacing during the absolute refractory period of a beat, the pacing stimulus prolongs or shortens the QT interval of that beat with respect to its preceding one in such a way that the morphology distinction between odd and even beats is diminished. Therefore, electrical impulses delivered during the absolute refractory period may decrease the amplitude of repolarization alternans. For example, if the QT interval is short or long, the pacing stimulus prolongs or shortens it, respectively.

The pacing stimulus is delivered by, for example, two active electrodes that belong to the same or different catheters or wires within the body. The wires may be pacing or defibrillation wires. The distance between two active electrodes is used to control the size of the pacing stimulus necessary to reduce or suppress repolarization alternans and decrease the likelihood or arrhythmia occurrence. If more than one pacing stimulus is delivered, such stimuli may be synchronous or asynchronous. These pacing stimuli may be delivered from active electrodes that are in the same or different catheters or wires.

By way of example, both active electrodes may be in the right ventricle, the coronary sinus, or the left ventricle. By way of another example, in one configuration, one active electrode is placed in the right ventricle and one in the coronary sinus. In another example, one active electrode may be placed in the left ventricle and one in the coronary sinus. Similarly, one active electrode may be placed in the right ventricle and one in the left ventricle.

At least five parameters may be used to determine whether a pacing stimulus may result in decrease of repolarization alternans: (i) the coupling of the pacing stimulus with respect to the R-wave; (ii) the amplitude of the pacing stimulus; (iii) the width, or duration, of the pacing stimulus; (iv) the physical separation, or distance, between the active electrodes that deliver the pacing stimulus; and (v) whether the pacing stimulus is delivered on an every even, every odd, or every beat basis.

When the level of repolarization alternans exceeds a threshold value over some period of time, such as one minute, therapy is delivered to suppress the repolarization alternans and, thus, reduce the likelihood that a heart rhythm disturbance will occur. The level of repolarization alternans estimated from electrocardiograms recorded from passive leads will differ, and, therefore, so will the level of decrease in the repolarization alternans following delivery of at least one pacing stimulus. The range of the pacing parameters (i)-(iv) above are used to define the pacing stimulus, and are calibrated to a level of repolarization alternans estimated from each pair of passive leads. In this manner, a calibrated electrical therapy plan that can be utilized to deliver appropriate electrical impulses to the patient's heart is produced.

The therapy is also delivered by the implanted device. For example the implantable device can incorporate the means for generating electrical stimulating pulses of specified energies and applying the pulses to body tissue at specified times, and deliver the impulses used for pacing the heart at the appropriate times and energy levels that are selected as described above.

The measured beat-to-beat variability in cardiac electrical activity, that is, the instantaneous measurement of RA, is used to identify periods when there is an increased probability that a heart rhythm disturbance may occur. For example, this measured variability is compared to a baseline level of RA measured, for example, before or after implantation of an ICD device, and prior to the patient's discharge from the hospital.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for preemptively suppressing a heart rhythm disturbance in a patient's heart with an implanted device configured to generate electrical impulses, the steps of the method comprising:
   a) detecting cardiac electrical signals from the patient's heart;
   b) measuring a beat-to-beat variability in the detected cardiac electrical signals and estimating at least one repolarization alternans parameter therefrom;
   c) determining a severity and likelihood of an imminent heart rhythm disturbance occurrence by comparing the at least one repolarization alternans parameter to a dynamically determined threshold value that is adaptively changed based on a noise level in the detected cardiac electrical signals, wherein the severity and likelihood of an imminent heart rhythm disturbance occurrence is characterized by a dynamically changing level of repolarization alternans in the detected cardiac electrical signals;
   d) calibrating an electrical therapy plan using the determined severity and likelihood of the imminent heart rhythm disturbance occurrence; and
   e) delivering appropriately calibrated electrical impulses to the patient's heart with the implanted device using the calibrated electrical therapy plan in order to preemptively suppress the severity and likelihood of the imminent heart rhythm disturbance occurrence.

2. The method as recited in claim 1 in which the at least one repolarization alternans parameter includes at least one of an alternans voltage, an alternans noise value, and a K-score.

3. The method as recited in claim 2 in which the dynamically determined threshold value is dependent on at least one of random noise and colored noise.

4. The method as recited in claim 3 in which step c) includes comparing the alternans voltage to an alternans voltage threshold value when the alternans noise value is at or below an alternans noise threshold value, and comparing the alternans voltage to a different alternans voltage threshold value when the alternans noise value is above the alternans noise threshold value.

5. The method as recited in claim 4 in which the alternans voltage threshold value is 1.9 microvolts, the alternans noise threshold value is 1.8 microvolts, and the different alternans voltage threshold value is a variable threshold value that applies a scale factor to the alternans noise value.

6. The method as recited in claim 1 in which step b) includes identifying abnormal heart beats using the cardiac electrical signals and forming a beat sequence with a predetermined number of selected heart beats, the selected heart beats not including the identified abnormal heart beats.

7. The method as recited in claim 6 in which cardiac electrical signals associated with abnormal heart beats are identified by at least one of:
   comparing a cross-correlation between a QRS complex of each heart beat with a template QRS complex formed from a predetermined number of heart beats in order to determine whether the cross-correlation is less than a threshold value; and
   comparing an R-to-R interval between each heart beat and a median R-to-R interval calculated from a predetermined number of heart beats immediately preceding each respective heart beat in order to determine whether the R-to-R interval is at least a selected percentage below the median R-to-R interval in formed beat sequence.

8. The method as recited in claim 6 in which step b) further includes replacing each abnormal beat with a replacement heart beat corresponding to a same portion of the cardiac electrical signal.

9. The method as recited in claim 8 in which the replacement cardiac electrical signal is at least one of an even median cardiac signal calculated from each cardiac signal in the beat sequence associated with an even-numbered beat and not identified as an abnormal heart beat; and an odd median cardiac signal calculated from each cardiac signal in the beat sequence associated with an odd-numbered beat and not identified as an abnormal heart beat.

10. The method as recited in claim 9 in which a cardiac electrical signal associated with an even-numbered abnormal heart beat is replaced with the even median cardiac signal, and a cardiac electrical signal associated with an odd-numbered abnormal heart beat is replaced with the odd median cardiac signal.

11. The method as recited in claim 6 in which when an abnormal heart beat is identified within a selected percentage from a middle of the beat sequence step c) includes estimating the electrical alternans parameter by:
 c)i) producing a power spectrum of the beat sequence by performing a fast Fourier transformation thereon; and
 c)ii) summing amplitudes of the power spectrum for frequencies beyond a prescribed alternans frequency.

12. The method as recited in claim 1 in which step c) includes determining and discriminating at least one of amplitudes and morphologies of even and odd beats in the measured cardiac electrical signals in at least one passive lead, and step d) includes using the discriminated at least one of amplitudes and morphologies in at least one passive lead to calibrate the electrical therapy plan such that delivered electrical impulses will disrupt a difference of at least one of amplitude and morphology between even and odd beats during alternans.

13. The method as recited in claim 1 in which the electrical impulses are delivered to the patient's heart by at least one pair of active electrodes, each of the active electrodes in the at least one pair of active electrodes being placed in locations selected from the group consisting of: a right ventricle of the patient's heart, a left ventricle of the patient's heart, a coronary sinus, a right atrium of the patient's heart, and combinations thereof.

14. The method as recited in claim 1 in which the electrical impulses delivered in step f) reduce an amplitude of the electrical alternans.

15. The method as recited in claim 1 in which step e) includes adjusting using the calibrated electrical therapy plan, at least one of an electrical impulse coupling with respect to an R-wave, an electrical impulse amplitude, an electrical impulse duration, and a separation between active electrodes selected to deliver the electrical impulses.

16. The method as recited in claim 1 in which the electrical impulses are delivered to the patient's heart on at least one of an every even, an every odd, and an every heart beat basis in order to decrease an amplitude of the electrical alternans.

17. A method for preemptively suppressing a heart rhythm disturbance in a patient's heart with an implanted device configured to generate electrical impulses, the steps of the method comprising:
 a) identifying optimal locations in a patient's heart at which a probability of detecting repolarization alternans is maximized;
 b) detecting cardiac electrical signals from the patient's heart using at least one pair of passive leads connected to the implanted device and placed in a body of the patient at the identified optimal locations;
 c) measuring a beat-to-beat variability in the detected cardiac electrical signals;
 d) determining a severity and likelihood of an imminent heart rhythm disturbance occurrence indicated by a level of repolarization alternans that is based on the measured beat-to-beat variability;
 e) calibrating an electrical therapy plan using the determined severity and likelihood of the imminent heart rhythm disturbance occurrence; and
 f) delivering appropriately calibrated electrical impulses to the patient's heart with the implanted device using the calibrated electrical therapy plan in order to preemptively suppress the severity and likelihood of the imminent heart rhythm disturbance occurrence.

18. The method as recited in claim 17 in which the at least one pair of passive leads includes two passive electrodes, each passive electrode being placed in locations selected from the group consisting of: a right ventricle of the patient's heart; a left ventricle of the patient's heart; a coronary sinus of the patient's heart; and combinations thereof.

19. The method as recited in claim 17 in which the at least one pair of passive leads includes three pairs of passive leads; the first pair of passive leads including one passive electrode placed in a right ventricle of the patient's heart and one passive electrode placed in a distal coronary sinus; the second pair of passive leads including one passive electrode placed in the right ventricle of the patient's heart and one passive electrode placed in a proximal coronary sinus; and the third pair of passive leads including one passive electrode placed in the distal coronary sinus and one passive electrode placed in the proximal coronary sinus.

20. The method as recited in claim 17 in which the at least one pair of passive leads includes three pairs of passive leads; the first pair of passive leads including one passive electrode placed in a left ventricle of the patient's heart and one passive electrode placed in a distal coronary sinus; the second pair of passive leads including one passive electrode placed in the left ventricle of the patient's heart and one passive electrode placed in one of a proximal coronary sinus and a left atrium of the patient's heart; and the third pair of passive leads including one passive electrode placed in the distal coronary sinus and one passive electrode placed in one of the proximal coronary sinus and the left atrium of the patient's heart.

* * * * *

UNITED STATES PATENT AND TRADEMARK OFFICE
CERTIFICATE OF CORRECTION

PATENT NO. : 9,931,049 B2  
APPLICATION NO. : 13/509390  
DATED : April 3, 2018  
INVENTOR(S) : Antonis Armoundas et al.

Page 1 of 1

It is certified that error appears in the above-identified patent and that said Letters Patent is hereby corrected as shown below:

In the Specification

Column 10, Line 42, "$v_n$" should be --$\mu_n$--.

Signed and Sealed this  
Fifteenth Day of May, 2018

Andrei Iancu  
*Director of the United States Patent and Trademark Office*